United States Patent
Khanna et al.

(10) Patent No.: US 8,466,340 B2
(45) Date of Patent: Jun. 18, 2013

(54) MOUSE MODEL FOR POMPE DISEASE AND METHODS OF USE THEREOF

(75) Inventors: Richie Khanna, Piscataway, NJ (US); Matthew J. Toth, Iselin, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 13/202,045

(22) PCT Filed: Feb. 16, 2010

(86) PCT No.: PCT/US2010/024262
§ 371 (c)(1),
(2), (4) Date: Nov. 30, 2011

(87) PCT Pub. No.: WO2010/096369
PCT Pub. Date: Aug. 26, 2010

(65) Prior Publication Data
US 2012/0064545 A1 Mar. 15, 2012

Related U.S. Application Data

(60) Provisional application No. 61/153,533, filed on Feb. 18, 2009.

(51) Int. Cl.
*A01K 67/00* (2006.01)
*G01N 33/00* (2006.01)

(52) U.S. Cl.
USPC ................................... 800/18; 800/8; 800/3

(58) Field of Classification Search
USPC .................................................... 800/18, 8, 3
See application file for complete search history.

(56) References Cited

U.S. PATENT DOCUMENTS

2004/0203096 A1  10/2004  Raben et al.
2006/0264467 A1  11/2006  Mugarage et al.

OTHER PUBLICATIONS

International Search Report and Written Opinion for PCT/US2010/024262, mailed Apr. 2, 2010.

*Primary Examiner* — Marcia S Noble
(74) *Attorney, Agent, or Firm* — SorinRand LLP

(57) ABSTRACT

The present invention provides mouse models for Pompe disease and methods of using the same to test agents that may be effective in the treatment of Pompe disease.

11 Claims, 9 Drawing Sheets

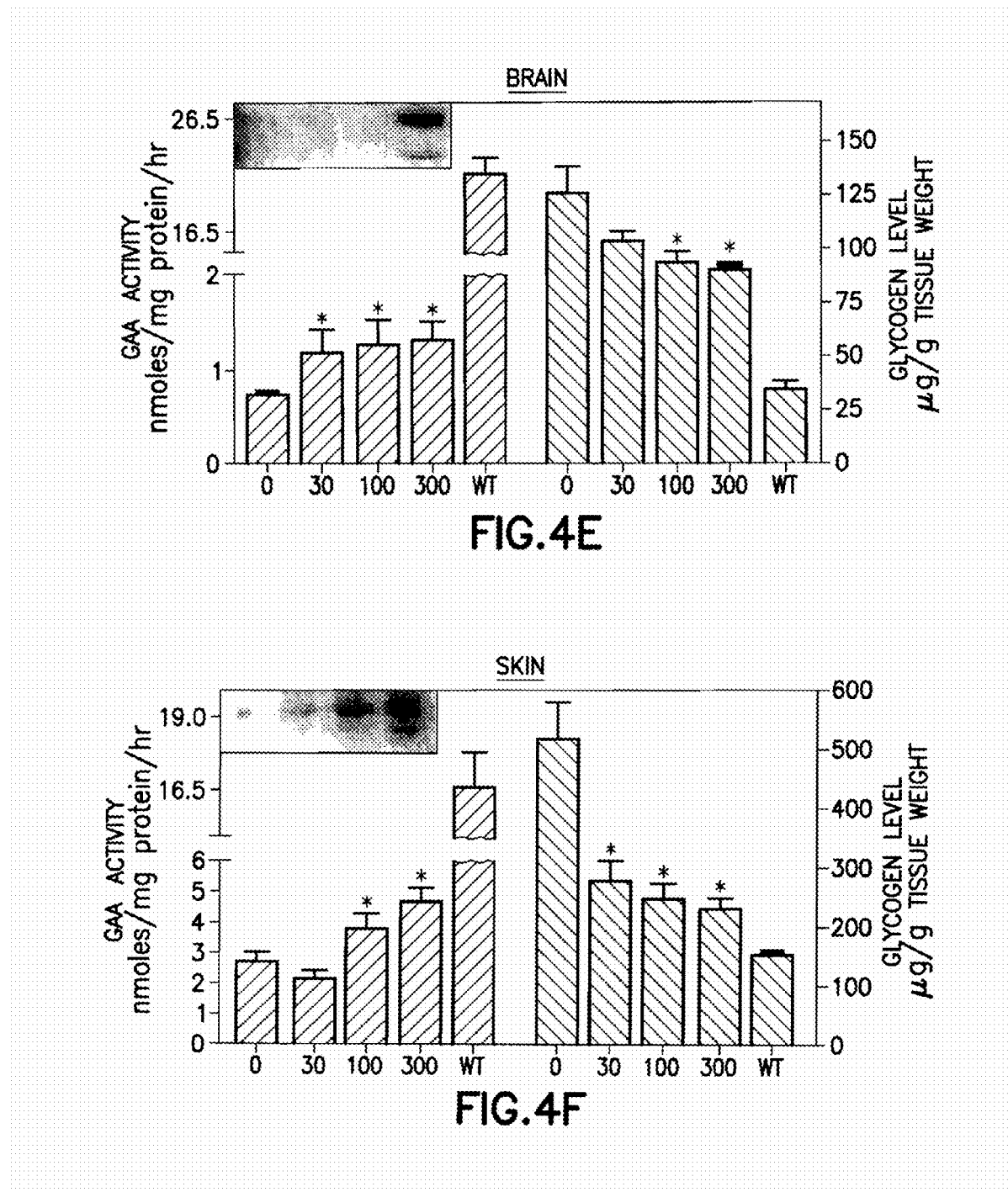

MOUSE MODEL FOR POMPE DISEASE AND METHODS OF USE THEREOF

CROSS-REFERENCE TO RELATED APPLICATIONS

This application is the National Stage of International Application No. PCT/US2010/024262, which designates the U.S., filed Feb. 16, 2010 which claims the benefit of U.S. Provisional Patent Application No. 61/153,533, filed Feb. 18, 2009, the contents of which are incorporated by reference herein.

FIELD OF THE INVENTION

The present invention provides mouse models for Pompe disease and methods of using the same to test agents that may be effective in the treatment of Pompe disease.

BACKGROUND OF THE INVENTION

Pompe disease (also known as glycogen storage disease type II (GSD-II), glycogenosis II, acid maltase deficiency (AMD), acid alpha-glucosidase deficiency, and lysosomal alpha-glucosidase deficiency) is an inherited lysosomal storage disorder caused by deficiency of an enzyme called acid α-glucosidase (GAA). The role of GAA within the body is to break down glycogen, the form of sugar stored in living cells for use as energy. Reduced or absent levels of GAA activity leads to the accumulation of glycogen in the affected tissues, including the heart, skeletal muscles (including those involved with breathing), liver, and nervous system. This accumulation of GAA is believed to cause progressive muscle weakness and respiratory insufficiency in individuals with Pompe disease. Pompe disease can occur in infants, toddlers, or adults, and the prognosis varies according to the time of onset and severity of symptoms. It is estimated that Pompe disease affects approximately 5,000 to 10,000 people worldwide.

There is a need for a mouse model to study Pompe disease and to test agents that may be effective in the treatment of Pompe disease.

SUMMARY OF THE INVENTION

The present invention provides mouse models for Pompe disease that are useful to study Pompe disease as well as to test agents that may be effective in the treatment of Pompe disease. In particular, the present invention provides a knockout transgenic mouse wherein the endogenous alpha-glucosidase gene is disrupted such that the knockout transgenic mouse substantially lacks the capacity to express the gene for mouse alpha-glucosidase and whose genome comprises at least one mutation in a gene encoding human alpha-glucosidase wherein at least one of: the amount of alpha-glucosidase protein and the level of alpha-glucosidase activity in at least one disease-relevant tissue of the knockout transgenic mouse is lower than a wild-type mouse. Likewise, the present invention provides a knockout transgenic mouse wherein the endogenous alpha-glucosidase gene is disrupted such that the knockout transgenic mouse substantially lacks the capacity to express the gene for mouse alpha-glucosidase and whose genome comprises at least one mutation in a gene encoding human alpha-glucosidase wherein the level of glycogen in at least one disease-relevant tissue of the knockout transgenic mouse is higher than a wild-type mouse.

In addition, the present invention provides methods of screening for a therapeutic agent for Pompe disease, comprising administering a test agent to a knockout transgenic mouse provided herein and evaluating the effect of the test agent on at least one of: the amount of alpha-glucosidase protein, the level of alpha-glucosidase activity or the level of glycogen in at least one disease-relevant tissue of the knockout transgenic mouse, wherein at least one of: an increase in the amount of alpha-glucosidase protein, an increase in the level of alpha-glucosidase activity or a reduction in the level of glycogen in at least one disease-relevant tissue relative to a similar knockout transgenic mouse that does not receive the test agent indicates the test agent is therapeutic for Pompe disease. The present invention also provides methods for assessing one or more agents for the treatment of Pompe disease, comprising administering one or more agents to a knockout transgenic mouse provided herein and evaluating the effect of the agents on at least one of: the amount of alpha-glucosidase protein, the level of alpha-glucosidase activity or the level of glycogen in at least one disease-relevant tissue of the knockout transgenic mouse, wherein at least one of: an increase in the amount of alpha-glucosidase protein, an increase in the level of alpha-glucosidase activity or a reduction in the level of glycogen in at least one disease-relevant tissue as compared to a similar knockout transgenic mouse that does not receive one or more agents is therapeutic for Pompe disease. In one embodiment, one or more agents is a pharmacological chaperone, a recombinant alpha glucosidase, an antineoplastic agent, an antirheumatic agent, a reproductive control agent, or any combination of two or more thereof. In one embodiment, one or more agents is DNJ, recombinant alpha glucosidase, Cyclophosphamide, Methotrexate, Rituximab, or any combination of two or more thereof. In one embodiment, one or more agents includes DNJ and recombinant alpha glucosidase. In one embodiment, one or more agents includes DNJ.

In one embodiment, at least one mutation is a missense mutation. In one embodiment, at least one mutation is P545L, P285R, E262K, E579K, or a combination of two or more thereof. In one embodiment, at least one mutation is P545L.

In one embodiment, the amount of alpha-glucosidase protein or the level of alpha-glucosidase activity in at least one disease-relevant tissue of the knockout transgenic mouse is in a range of about 3% to about 10% relative to that of a wild-type mouse.

In one embodiment, the level of glycogen in at least one disease-relevant tissue of the knockout transgenic mouse is at least 2-fold higher than that of a wild-type mouse.

BRIEF DESCRIPTION OF THE DRAWINGS

FIG. 4E illustrates the GAA and glycogen levels in a sample from brain tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ as well as wild-type (WT) mice which were not dosed with DNJ. In addition, the inset illustrates the level of GAA protein detected by Western blotting in a sample from brain tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ.

FIG. 4F illustrates the GAA and glycogen levels in a sample from skin tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ as well as wild-type (WT) mice which were not dosed with DNJ. In addition, the inset illustrates the level of GAA protein detected by Western blotting in a sample from skin tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ.

DETAILED DESCRIPTION OF THE INVENTION

Figure 1B:
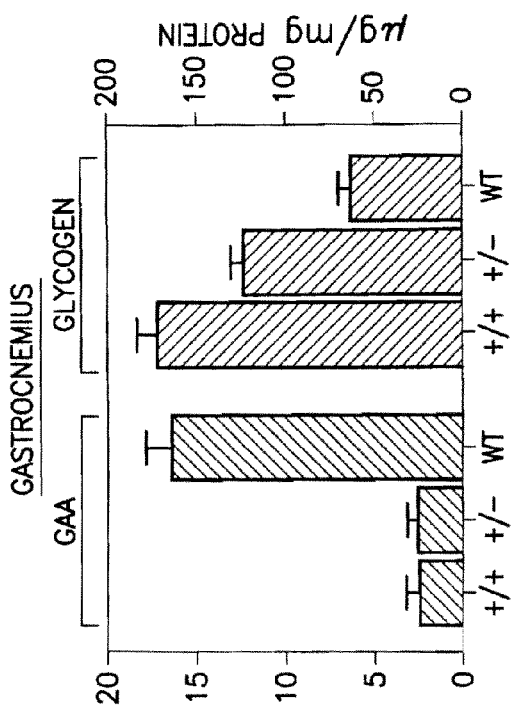
FIG. 1B illustrates the GAA and glycogen levels in a sample from gastrocnemius tissue of hP545L GAA Tg/KO mice expressing "Moderate" GAA levels having genotype Tg+/+, Tg+/− as well as wild-type (WT) mice.

As used herein the following terms shall have the definitions set forth below.

As used herein the term "treatment" means to mitigate or ameliorate one or more symptoms associated with Pompe disease.

As used herein the phrase "disease-relevant tissue" means a tissue that displays biochemical or histological pathology associated with Pompe disease, (e.g., an increase in glycogen level relative to tissue that is not pathologic for Pompe disease, or the lysosomal component thereof). Exemplary disease-relevant tissue includes that from heart, diaphragm, gastrocnemius, soleus, brain and skin.

Two new Pompe transgenic mouse lines were created that express "Moderate" (10%) and "Low" (3%) levels of hP545L GAA, a mutant form of the human enzyme. GAA levels in disease relevant tissues including heart, diaphragm, skeletal muscles, skin and brain of 12-week old 'Low' and 'Moderate' hP545L GAA Tg/KO mouse lines were, on average, 3% and 10% of the levels seen in wild-type littermates, respectively. Importantly, 12-week old 'Low' and 'Moderate' hP545L GAA Tg/KO mice showed accumulation of glycogen, with 6-10 and 2-3-fold higher levels than wild-type littermates, respectively. Four-week oral administration (ad libitum) of DNJ to 'Moderate' hP545L GAA Tg/KO mice resulted in a significant and dose-dependent increase in tissue GAA activity, protein levels, and processing as well as a concomitant decrease in tissue glycogen levels.

Additionally, both daily and less-frequent dosing regimens (i.e., (i) 3 days on/4 days off; (ii) 5 days on/2 days off; or (iii) 7 days on/7 days off) of DNJ to hP545L GAA Tg/KO mice expressing "Moderate" GAA levels led to a significant reduction in glycogen levels in disease-relevant tissue. In fact, less-frequent dosing regimens resulting in greater glycogen reduction compared to daily dosing.

Though not meant to be bound by theory, it is believed that on/off DNJ dosing regimens exploit the difference in half-life of DNJ (hours) compared to GAA (days). In particular, the "on" period of DNJ provides a period of enhanced protein stabilization and trafficking to lysosomes (maximal chaperone effect) followed by the "off" period of DNJ which allows for dissociation and tissue clearance of the chaperone (providing maximal in situ enzyme activity). The "on/off" DNJ dosing regimens thereby result in a larger net gain in cellular GAA activity than daily dosing of DNJ. Importantly, less-frequent dosing regimens of DNJ also utilize less drug than daily dosing which is beneficial to patients as it is more cost-effective.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Mouse Model with Human GAA Mutation

To develop mouse models of Pompe disease, a human GAA gene containing a mutation is introduced (i.e., a transgene) into a mouse substantially lacking the capacity to express endogenous GAA (i.e., a knockout). It is understood that any mutation in the human GAA gene that leads to an increase in the level of glycogen accumulation in a cell would provide a transgene useful in the creation of mouse models for Pompe disease.

As many individuals with Pompe disease have missense mutations in the GAA gene, missense mutations in the human GAA gene were screened for their use as a transgene. It is believed that missense mutations alter the structure of GAA, resulting in the accumulation and/or degradation of this enzyme in the endoplasmic reticulum (ER). As a result of the accumulation and/or degradation of GAA in the ER, GAA is unable to reach the lysosome, the part of the cell where GAA breaks down glycogen. It is believed that certain agents, termed "pharmacological chaperones" bind to GAA in the ER and assist the GAA in exiting the ER such that the GAA is able to reduce the level of glycogen present in the cell. For example, an agent currently in Phase II clinical studies for the treatment of Pompe disease, 1-deoxynojirimycin-HCl (DNJ, also known as AT2220), is believed to act as a pharmacological chaperone for GAA. Note that the present invention is not intended to be bound by the aforementioned mechanism.

DNJ has been shown to increase GAA activity, GAA protein levels, and GAA processing to the mature form of GAA both in vitro and in vivo. In particular, DNJ has been shown to significantly increase the level of multiple different mutant forms of GAA in Pompe patient-derived fibroblasts and COS-7 cells transiently-transfected with recombinant human GAA (data not shown). Likewise, DNJ has been shown to directly bind to GAA and cause a concentration-dependent increase in the thermostability of recombinant human GAA in vitro (data not shown). In addition, DNJ has been shown to increase the level of GAA activity as well as GAA protein levels and GAA processing to the 95-, 76-, and 70-kDa forms in HEK293 cells transiently-transfected with a mutated form of GAA (including M519V, P545L, G549R, and L552P; data not shown). Furthermore, in vivo, GAA activity has been shown to increase in a dose-dependent manner in both mice and cynologous monkeys administered DNJ orally (data not shown). Likewise, DNJ increased GAA protein levels and processing to the 70-kDa mature form of GAA in both mice and cynologous monkeys (data not shown). Such increase in activity is believed to be specific for GAA, as no increase was observed in two other lysosomal enzymes examined in mice administered DNJ, specifically alpha-galactosidase and beta-glucocerebrosidase (data not shown).

To further study the effects of DNJ on Pompe disease, mouse models were created containing a mutation known to be responsive to DNJ. It is understood that the mouse model of Pompe disease provided herein is useful for the study of Pompe disease as well as for the identification of other agents that may be useful in the treatment of Pompe disease. Likewise, it is understood that the principles taught herein may be applied to the creation of other mouse models that are responsive to other agent(s) as well as the study of Pompe disease and the identification of other agents that may be useful in the treatment of Pompe disease.

Identification of Human GAA Mutation Responsive to DNJ

In vitro studies were conducted to identify a human GAA missense mutation responsive to the agent (DNJ). Out of several mutations initially examined (IVS1AS, T>G,-13, D654E, V8161, T927I, P545L, M519V, W402R), the P545L (proline 545 leucine substitution) mutation was chosen as it showed a robust, reproducible, dose-dependent and statistically-significant increase in GAA activity after 5-day incubation with DNJ (data not shown). However, other human GAA missense mutations which are even more responsive than P545L to DNJ have subsequently been identified in vitro (including P285R, E262K, E579K; data not shown). Such mutations are also suitable for the generation of transgenic mice for testing DNJ as well as other agents that may be useful in the treatment of Pompe disease.

Generation of hP545L GAA Transgenic/Knockout

The generation of transgenic (Tg) mice were similar to those described previously for Fabry transgenic mice by Shimmoto et al., "Generation and characterization of transgenic mice expressing a human mutant alpha-galactosidase with an R301Q substitution causing a variant form of Fabry disease," *FEBS Lett,* 417(1):89-91 (1997) and Ishii et al., "Transgenic mouse expressing human mutant alpha-galactosidase A in an endogenous enzyme deficient background: a biochemical animal model for studying active-site specific chaperone therapy for Fabry disease," *Biochim Biophys Acta,* 1690(3):250-7 (2004) (both of which are incorporated herein by reference), with the exception that the transgene used was human P545L GAA (SEQ ID NO: 1). Briefly, the P545L mutation was introduced in a human GAA gene (SEQ ID NO: 3) using polymerase chain reaction (PCR) mutagenesis. The resultant mutant human GAA gene was cloned into a pCl mammalian expression vector containing a cytomegalovirus (CMV) promoter at Kpn I and Sal I restriction sites. This transgenic construct was then used for generating founder mice at contract research organization (CRO) Xenogen Corporation (Cranbury, N.J.) using routine methodologies described previously by Gordon et al., "Genetic transformation of mouse embryos by microinjection of purified DNA," *Proc Natl Aced Sci USA,* 77(12):7380-4 (1980), incorporated herein by reference. Briefly, the vector carrying the transgene was first injected in the pronuclei of mouse oocyte followed by insemination in super-ovulated wild-type C57BU6 female mice. The pups obtained were screened for the presence of transgene by PCR amplification of tail genomic DNA. Two founder mice were obtained both carrying, a 500 bp fragment amplified using 5'-TACGTATTAGTCATCGCTAT-3' (SEQ ID NO: 5) forward and 5'-ATTAAGTACTCTAGCCTTAA-3' (SEQ ID NO: 6) reverse primers. The PCR amplification consisted of 30 cycles of denaturation at 94° C. for 30 seconds, annealing at 55° C. for 1 min. and elongation at 72° C. for 2 min. The founder mice were bred separately with wild-type C57BL/6 mice to obtain two transgenic F1 mouse lines on a wild-type GAA background [Tg (+/−) mGAA (+/+)]. The F1 transgenic lines were then bred with Pompe knockout (KO) mice described in Raben et al., "Targeted disruption of the acid alpha-glucosidase gene in mice causes an illness with critical features of both infantile and adult human glycogen storage disease type II," *J Biol Chem,* 273(30):19086-19092 (1988), incorporated herein by reference (kind gift of Dr. Barry Byrne). The resultant pups were screened for the presence of transgene by PCR amplification using the primers described above as well as the KO alleles as described by Raben et al. (Raben et al., "Targeted disruption of the acid alpha-glucosidase gene in mice causes an illness with critical features of both infantile and adult human glycogen storage disease type II," *J Biol Chem,* 273(30):19086-19092 (1988)). Following multiple crossovers, each of the two aforementioned F1 transgenic lines gave mice with 4 different genotypes. These mice were either homozygous for hP545L trangene [Tg (+/+) KO (−/−)], heterozygous [Tg (+/−) KO (−/−)], no transgene [Tg (−/−) KO (−/−)] or carried wild-type [Tg (−/−) KO (+/+)]. The two homozygous transgenic lines expressed either 1 or 10 copies of the transgene designated as 'Low' and 'Moderate,' respectively. The mice were characterized further for their biochemical phenotype (using the assays described below) as well as to test the efficacy of DNJ in vivo.

Preparation of Plasma and Tissue for Assays

Mice were euthanized with $CO_2$ and body weights were recorded. Whole blood was drawn into lithium heparin tubes from the inferior vena cava after $CO_2$ euthanization. Plasma was collected by spinning blood at 2700 g for 10 minutes at 4° C. Heart, diaphragm, gastrocnemius, soleus, skin, and brain tissues were removed, washed in cold PBS, blotted dry, and weighed before storing on dry ice. For biochemical assays (GAA activity, glycogen and Western blotting), lysates were prepared by homogenizing ~50 mg tissue for 3-5 seconds on ice with a micro homogenizer in 200 µL Lysis Buffer (25 mM Bis-Tris pH 6.5, 150 mM NaCl, 1% Triton X-100 pH 6.5). For histology assays, tissues were harvested and fixed immediately in 3.7% Formaldehyde/90% Ethanol mix. After fixation, the samples were processed in various grades (10, 20, 50, 75, 100%) of alcohol and embedded in paraffin.

Biochemical Assay for Determining GAA Level

Twenty µL of lysate were added to 50 µL Assay buffer containing 3 mM 4-MU-α-D-glucopyranoside (4-MUG) in 50 mM potassium acetate buffer (pH 4.0), and incubated for 1 hour at 37° C. Seventy µL of Stop Solution (0.4 M glycine, pH 10.8) were then added and fluorescence read on a Victor$^3$ plate reader (Perkin Elmer, Waltham, Mass.) at 355 nm excitation and 460 nm emission and raw fluorescence counts were background subtracted (defined by counts from substrate solution only). A Micro BCA Protein Assay Kit (Pierce, Rockford, Ill.) was used according to the manufacturer's instructions to determine protein concentration in lysates. A 4-methylumbelliferone (4-MU) standard curve ranging from 1.3 nM to 30 µM was run each day for conversion of fluorescence data to absolute GAA activity. Data are ultimately expressed as nanomoles/milligram of protein/hour (nmol/mg protein/hr). For plasma GAA levels, exactly similar steps as above were followed except that no homogenization was required.

Figure 1D:
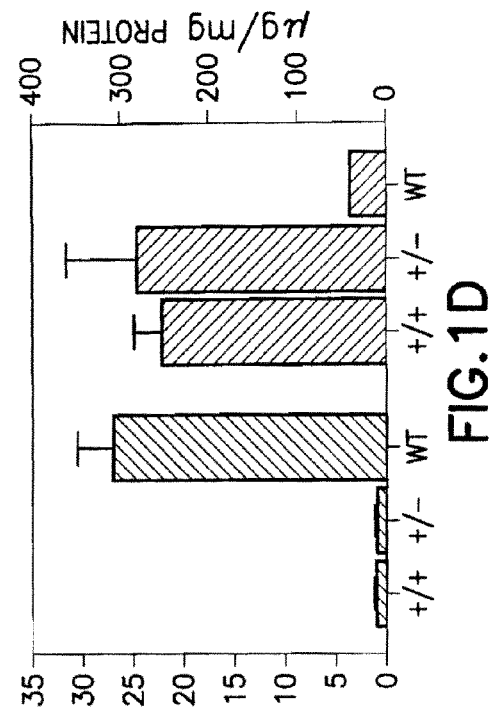
FIG. 1D illustrates the GAA and glycogen levels in a sample from gastrocnemius tissue of hP545L GAA Tg/KO mice expressing "Low" GAA levels having genotype Tg+/+, Tg+/− as well as wild-type (WT) mice.
Figure 1A:
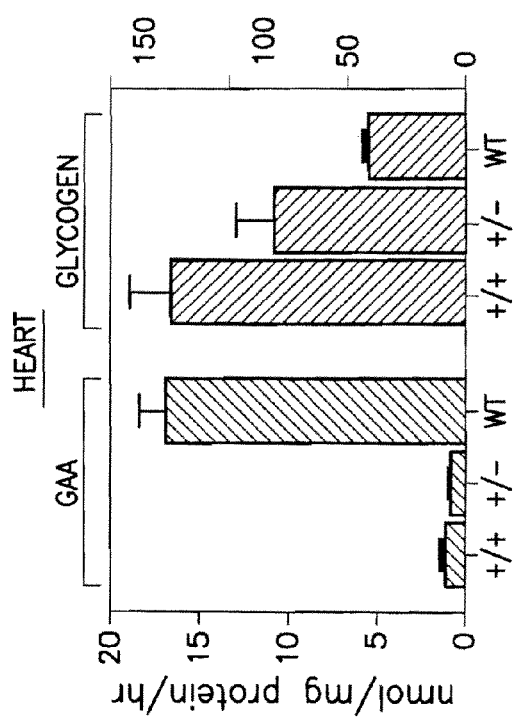
FIG. 1A illustrates the GAA and glycogen levels in a sample from heart tissue of hP545L GAA Tg/KO mice expressing "Moderate" GAA levels having genotype Tg+/+, Tg+/− as well as wild-type (WT) mice.
Figure 1C:
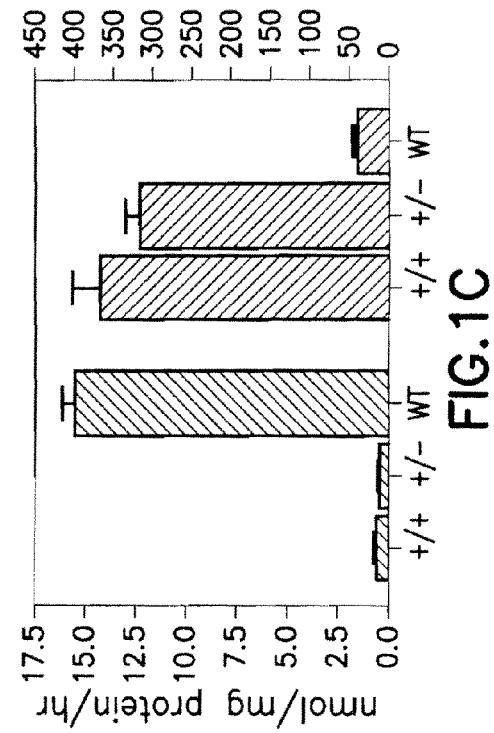
FIG. 1C illustrates the GAA and glycogen levels in a sample from heart tissue of hP545L GAA Tg/KO mice expressing "Low" GAA levels having genotype Tg+/+, Tg+/− as well as wild-type (WT) mice.
Figure 2A:
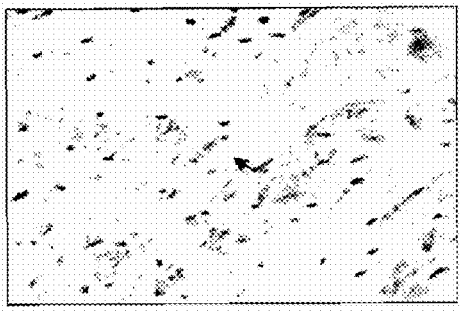
FIG. 2A illustrates a sample of heart tissue from hP545L GAA Tg/KO mice expressing "Moderate" GAA levels having genotype Tg+/+ immunohistologically stained for glycogen and magnified 20×.
Figure 2B:
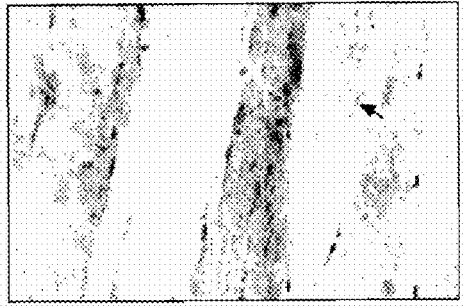
FIG. 2B illustrates a sample of gastrocnemius tissue from hP545L GAA Tg/KO mice expressing "Moderate" GAA levels having genotype Tg+/+ immunohistologically stained for glycogen and magnified 20×.
Figure 2C:
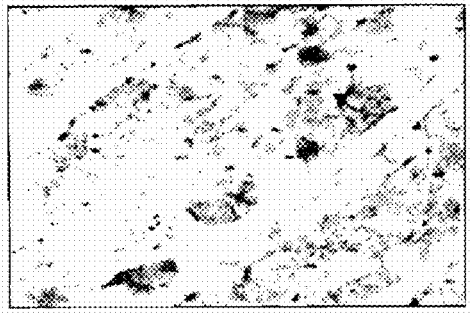
FIG. 2C illustrates a sample of heart tissue from hP545L GAA Tg/KO mice expressing "Low" GAA levels having genotype Tg+/+ immunohistologically stained for glycogen and magnified 20×.
Figure 2D:
FIG. 2D illustrates a sample of gastrocnemius tissue from hP545L GAA Tg/KO mice expressing "Low" GAA levels having genotype Tg+/+ immunohistologically stained for glycogen and magnified 20×.
Figure 2E:
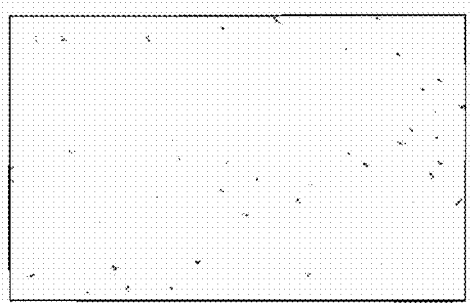
FIG. 2E illustrates a sample of heart tissue from wild-type mice immunohistologically stained for glycogen and magnified 20×.
Figure 2F:
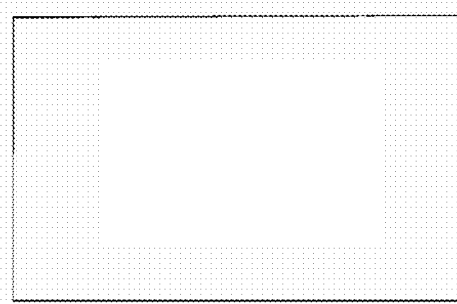
FIG. 2F illustrates a sample of gastrocnemius tissue from wild-type mice immunohistologically stained for glycogen and magnified 20×.
Figure 3A:
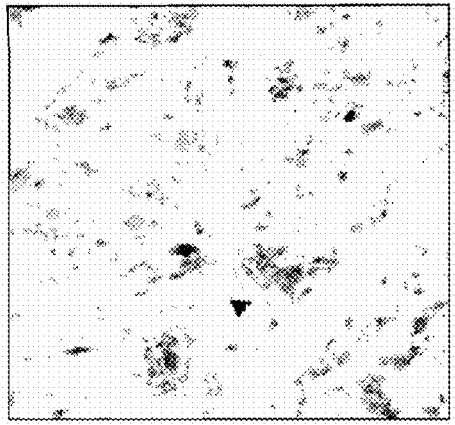
FIG. 3A illustrates a sample of heart tissue from hP545L GAA Tg/KO mice expressing "Moderate" GAA levels having genotype Tg+/+ immunohistologically stained with LAMP1 antibody and magnified 20×.
Figure 3B:
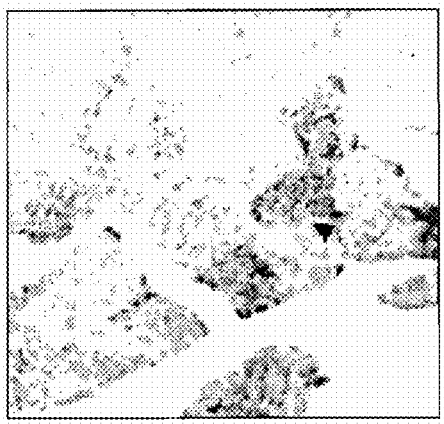
FIG. 3B illustrates a sample of gastrocnemius tissue from hP545L GAA Tg/KO mice expressing "Moderate" GAA levels having genotype Tg+/+ immunohistologically stained with LAMP1 antibody and magnified 20×.
Figure 3C:
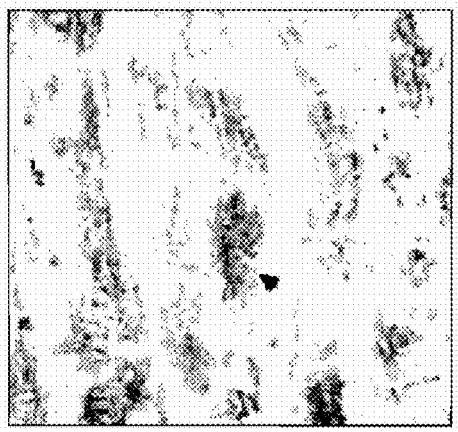
FIG. 3C illustrates a sample of heart tissue from hP545L GAA Tg/KO mice expressing "Low" GAA levels having genotype Tg+/+ immunohistologically stained with LAMP1 antibody and magnified 20×.
Figure 3D:
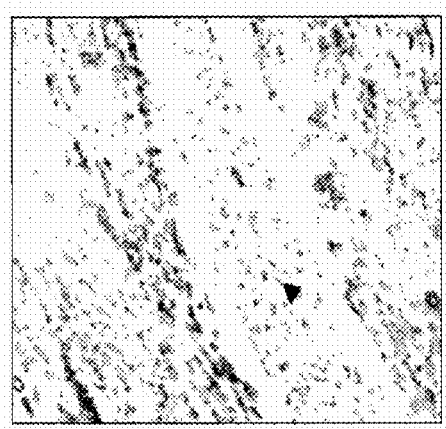
FIG. 3D illustrates a sample of gastrocnemius tissue from hP545L GAA Tg/KO mice expressing "Low" GAA levels having genotype Tg+/+ immunohistologically stained with LAMP1 antibody and magnified 20×.
Figure 3E:
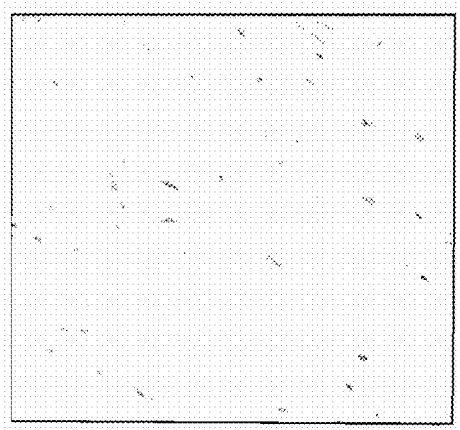
FIG. 3E illustrates a sample of heart tissue from wild-type mice immunohistologically stained with LAMP1 antibody and magnified 20×.
Figure 3F:
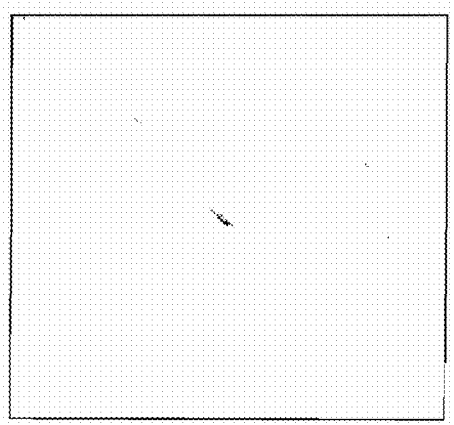
FIG. 3F illustrates a sample of gastrocnemius tissue from wild-type mice immunohistologically stained with LAMP1 antibody and magnified 20×.
Figure 4A:
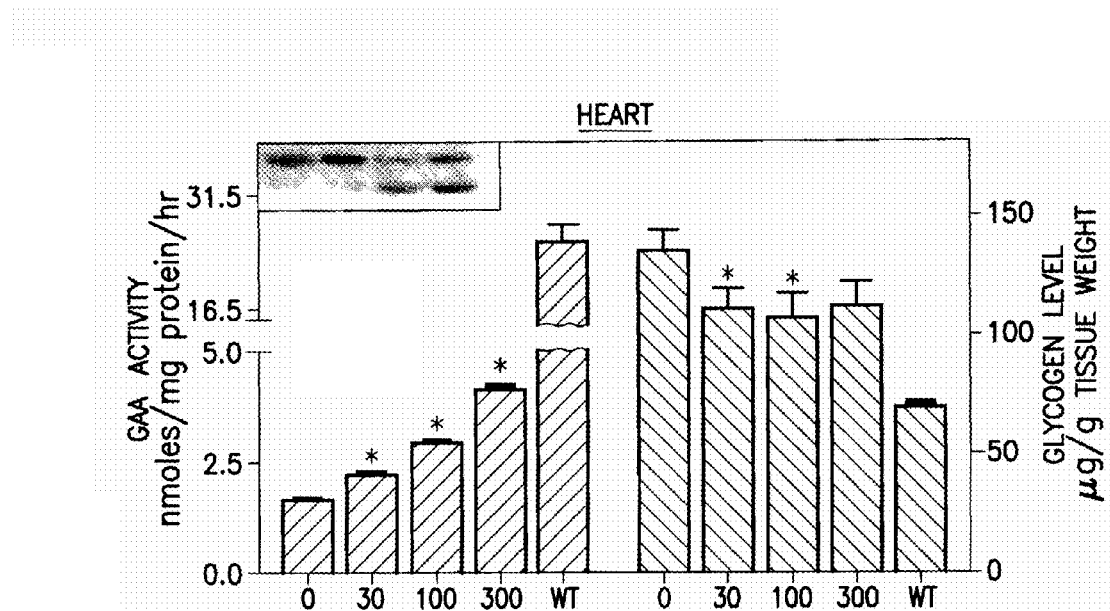
FIG. 4A illustrates the GAA and glycogen levels in a sample from heart tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ as well as wild-type (WT) mice which were not dosed with DNJ. In addition, the inset illustrates the level of GAA protein detected by Western blotting in a sample from heart tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ.
Figure 4B:
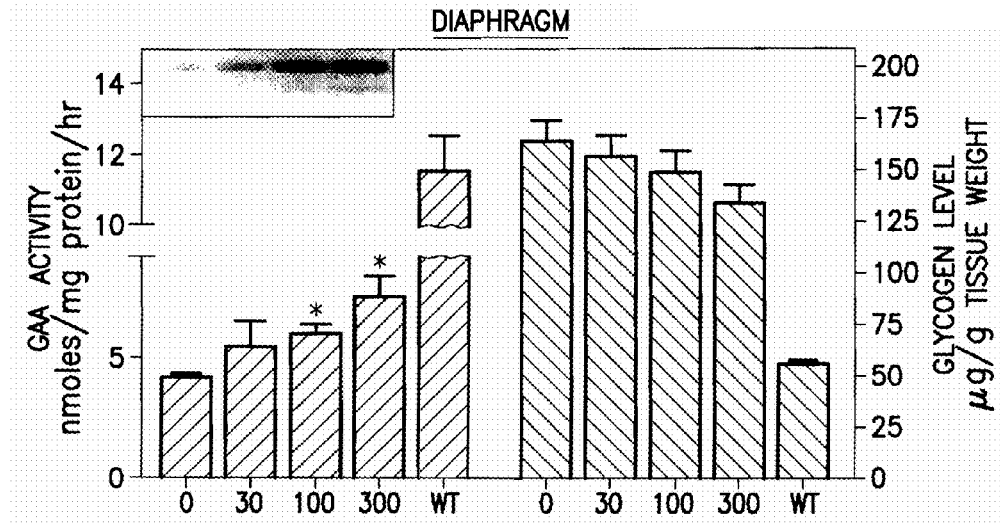
FIG. 4B illustrates the GAA and glycogen levels in a sample from diaphragm tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ as well as wild-type (WT) mice which were not dosed with DNJ. In addition, the inset illustrates the level of GAA protein detected by Western blotting in a sample from diaphragm tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ.
Figure 4C:
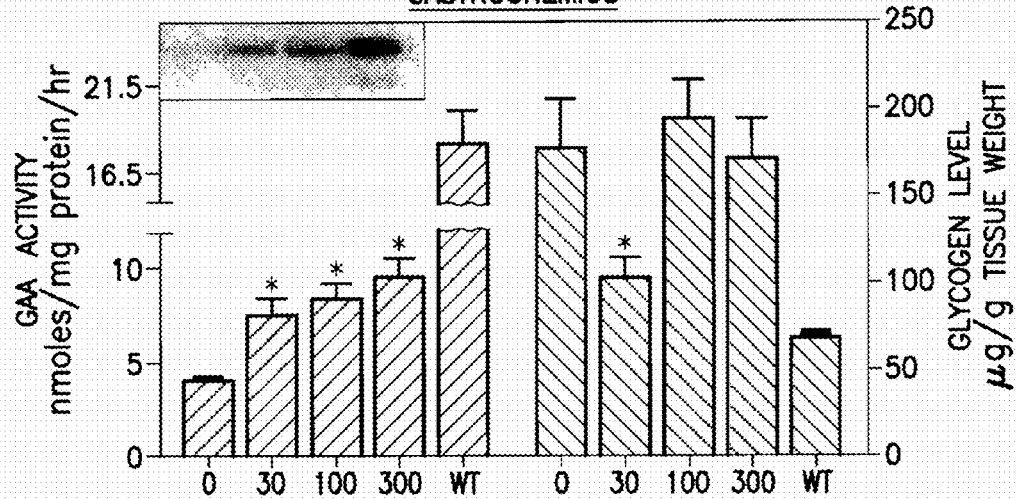
FIG. 4C illustrates the GAA and glycogen levels in a sample from gastrocnemius tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ as well as wild-type (WT) mice which were not dosed with DNJ. In addition, the inset illustrates the level of GAA protein detected by Western blotting in a sample from gastrocnemius tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ.
Figure 4D:
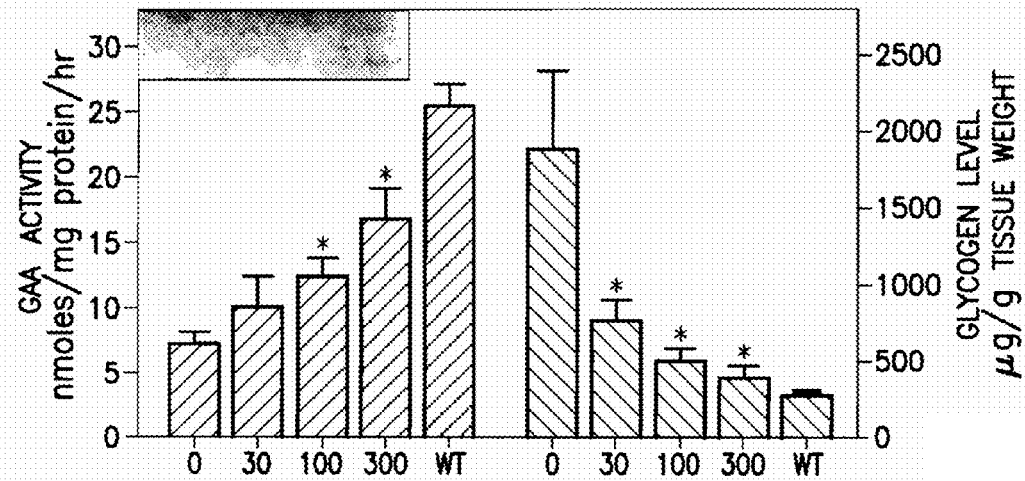
FIG. 4D illustrates the GAA and glycogen levels in a sample from soleus tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ as well as wild-type (WT) mice which were not dosed with DNJ. In addition, the inset illustrates the level of GAA protein detected by Western blotting in a sample from soleus tissue of hP545L GAA Tg/KO mice expressing "Moderate" GAA levels having genotype Tg+/+ which were in the control group (0 mg/kg/day DNJ) or orally dosed for 4 weeks with the aim of administering 30, 100, or 300 mg/kg/day free-base equivalent of DNJ.
Figure 5A:
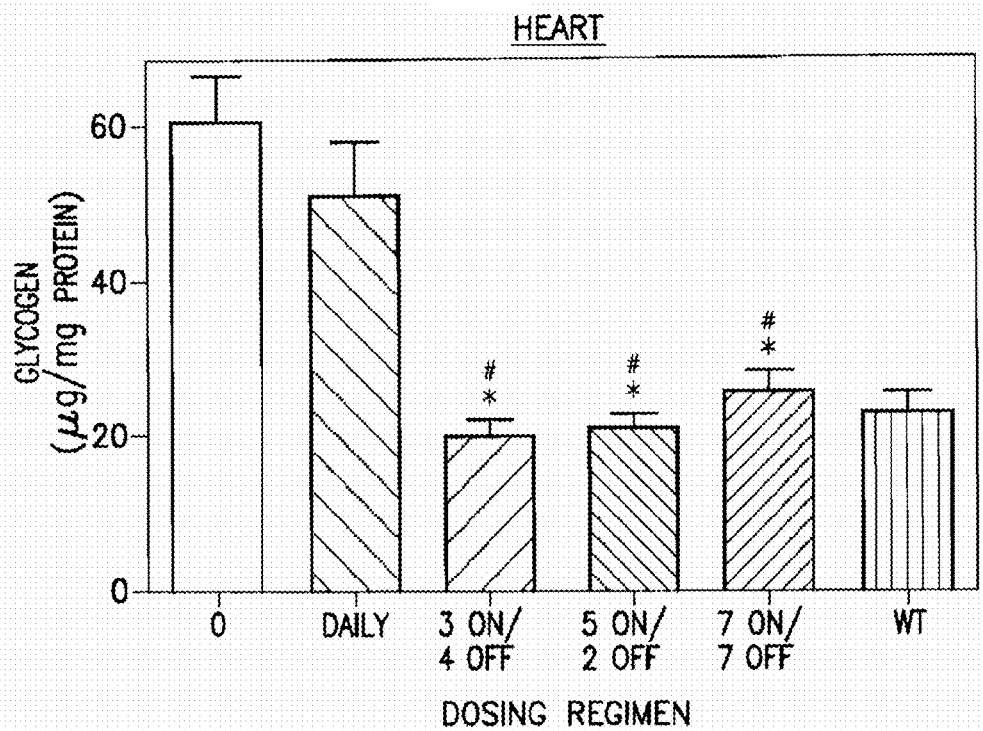
FIG. 5A illustrates the glycogen levels in a sample from heart tissue of hP545L GAA Tg/KO mice expressing "Moderate" GAA levels having genotype Tg+/+ which were in the control group (0 mg/kg/day DNJ), orally dosed (ad libitum in drinking water) with the aim of administering 100 mg/kg/day free-base equivalent of DNJ either daily or using one of three less-frequent on/off regimens (i) 3 days on/4 days off; (ii) 5 days on/2 days off; or (iii) 7 days on/7 days off) for 4 weeks as well as wild-type (WT) mice which were not dosed with DNJ. Each bar represents pooled data from two independent studies with the mean±SEM of 14 mice/group analyzed in triplicate.
Figure 5B:
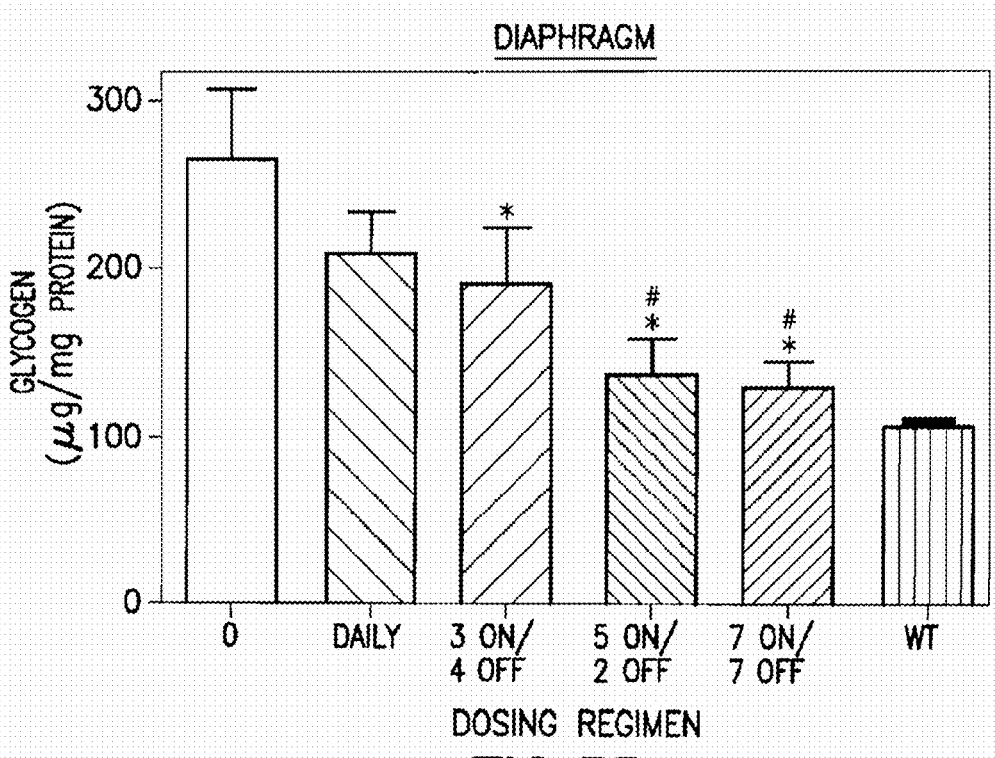
FIG. 5B illustrates the glycogen levels in a sample from diaphragm tissue of hP545L GAA Tg/KO mice expressing "Moderate" GAA levels having genotype Tg+/+ which were in the control group (0 mg/kg/day DNJ), orally dosed (ad libitum in drinking water) with the aim of administering 100 mg/kg/day free-base equivalent of DNJ either daily or using one of three less-frequent on/off regimens (i.e., (i) 3 days on/4 days off; (ii) 5 days on/2 days off; or (iii) 7 days on/7 days off) for 4 weeks as well as wild-type (WT) mice which were not dosed with DNJ. Each bar represents pooled data from two independent studies with the mean±SEM of 14 mice/group analyzed in triplicate.
Figure 5C:
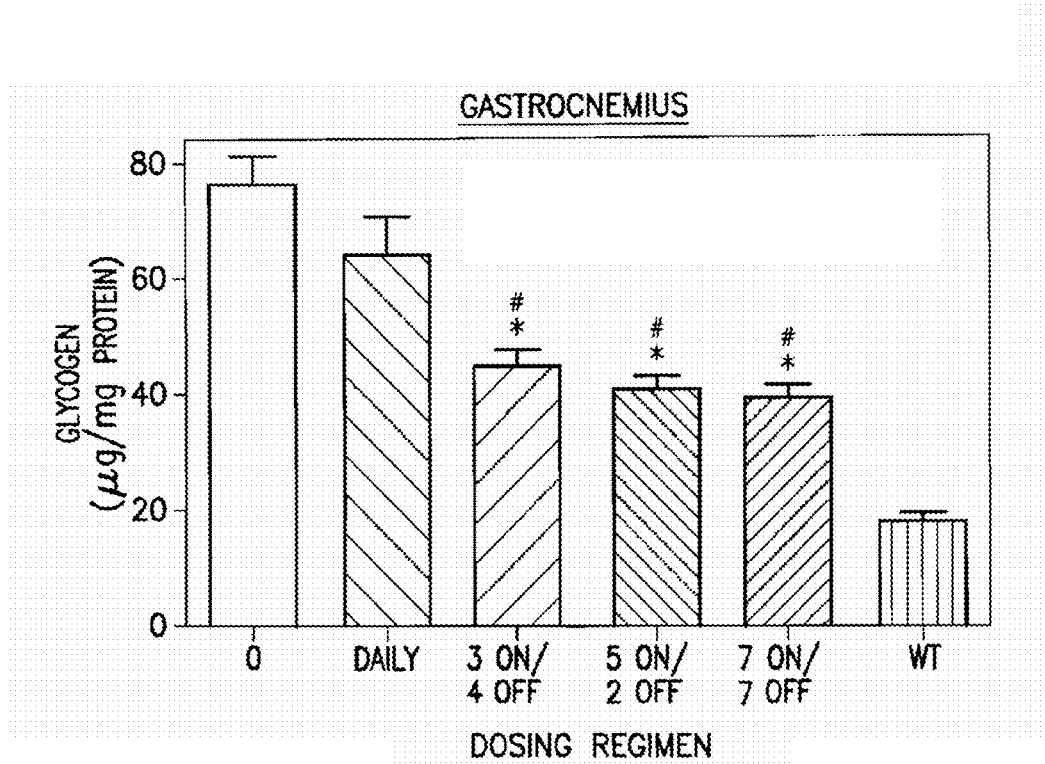
FIG. 5C illustrates the glycogen levels in a sample from gastrocnemius tissue of hP545L GAA Tg/KO mice expressing "Moderate" GAA levels having genotype Tg+/+ which were in the control group (0 mg/kg/day DNJ), orally dosed (ad libitum in drinking water) with the aim of administering 100 mg/kg/day free-base equivalent of DNJ either daily or using one of three less-frequent on/off regimens (i.e., (i) 3 days on/4 days off; (ii) 5 days on/2 days off; or (iii) 7 days on/7 days off) for 4 weeks as well as wild-type (WT) mice which were not dosed with DNJ. Each bar represents pooled data from two independent studies with the mean±SEM of 14 mice/group analyzed in triplicate.
Figure 5D:
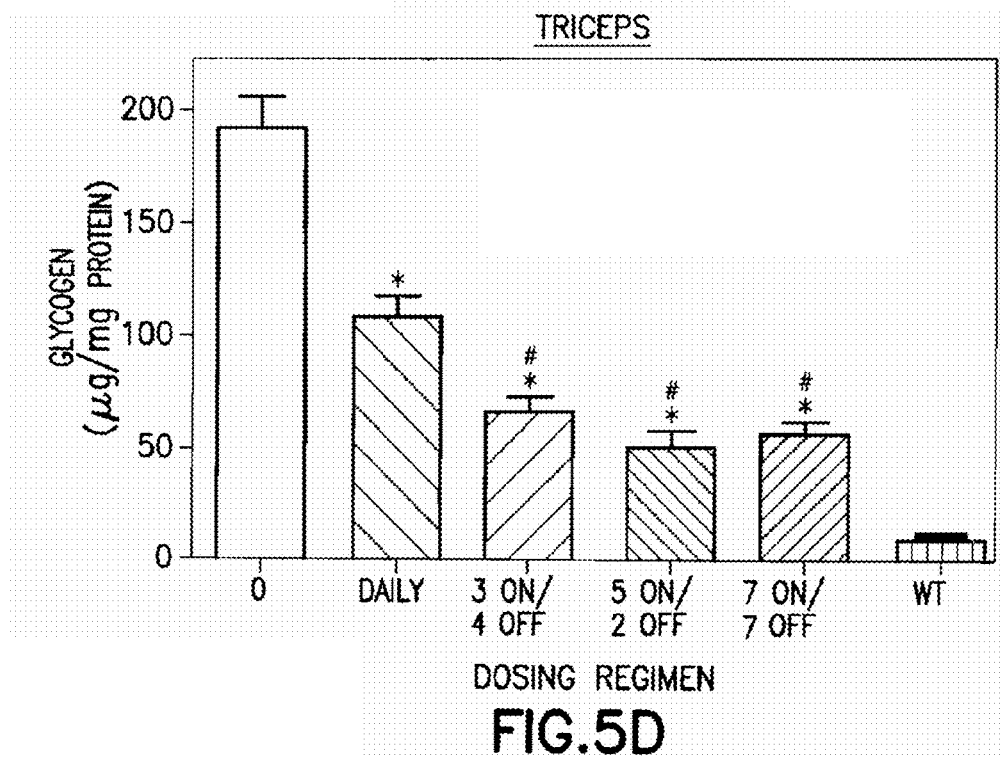
FIG. 5D illustrates the glycogen levels in a sample from triceps tissue of hP545L GAA Tg/KO mice expressing "Moderate" GAA levels having genotype Tg+/+ which were in the control group (0 mg/kg/day DNJ), orally dosed (ad libitum in drinking water) with the aim of administering 100 mg/kg/day free-base equivalent of DNJ either daily or using one of three less-frequent on/off regimens (i.e., (i) 3 days on/4 days off; (ii) 5 days on/2 days off; or (iii) 7 days on/7 days off) for 4 weeks as well as wild-type (WT) mice which were not dosed with DNJ. Each bar represents pooled data from two independent studies with the mean±SEM of 14 mice/group analyzed in triplicate.
Figure 5E:
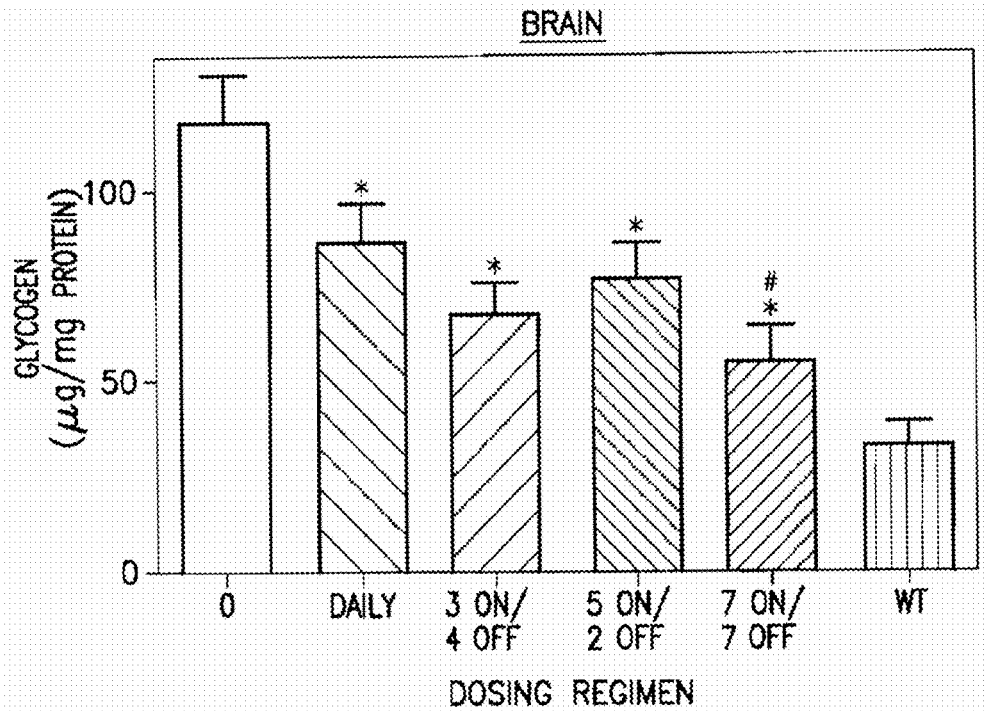
FIG. 5E illustrates the glycogen levels in a sample from brain tissue of hP545L GAA Tg/KO mice expressing "Moderate" GAA levels having genotype Tg+/+ which were in the control group (0 mg/kg/day DNJ), orally dosed (ad libitum in drinking water) with the aim of administering 100 mg/kg/day free-base equivalent of DNJ either daily or using one of three less-frequent on/off regimens (i.e., (i) 3 days on/4 days off; (ii) 5 days on/2 days off; or (iii) 7 days on/7 days off) for 4 weeks as well as wild-type (WT) mice which were not dosed with DNJ. Each bar represents pooled data from two independent studies with the mean±SEM of 14 mice/group analyzed in triplicate.
Figure 5F:
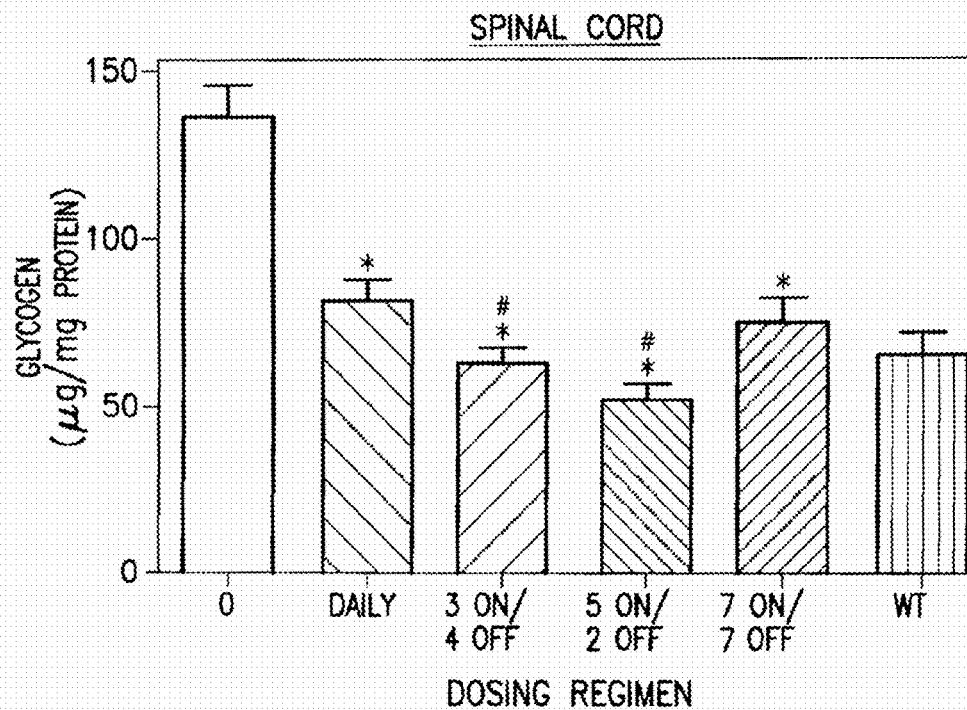
FIG. 5F illustrates the glycogen levels in a sample from spinal cord tissue of hP545L GAA Tg/KO mice expressing "Moderate" GAA levels having genotype Tg+/+ which were in the control group (0 mg/kg/day DNJ), orally dosed (ad libitum in drinking water) with the aim of administering 100 mg/kg/day free-base equivalent of DNJ either daily or using one of three less-frequent on/off regimens (i.e., (i) 3 days on/4 days off; (ii) 5 days on/2 days off; or (iii) 7 days on/7 days off) for 4 weeks as well as wild-type (WT) mice which were not dosed with DNJ. Each bar represents pooled data from two independent studies with the mean±SEM of 14 mice/group analyzed in triplicate.

As illustrated in FIGS. 1A and 1B, the GAA level (determined using the aforementioned assay) in samples from heart tissue and gastrocnemius tissue of hP545L GAA Tg/KO mice expressing "Moderate" GAA levels having genotype Tg+/+ or Tg+/− displayed ~10% of GAA levels as compared to wild-type (WT) mice. Likewise, as illustrated in FIGS. 1C and 1D, the GAA level (determined using the aforementioned assay) in samples from heart tissue and gastrocnemius tissue of hP545L GAA Tg/KO mice expressing "Low" GAA levels having genotype Tg+/+ or Tg+/− displayed ~3% of GAA levels as compared to wild-type (WT) mice.

Biochemical Assay for Determining Glycogen Level

Tissue glycogen levels were measured in supernatants of heat denatured (99° C. for 10 min.) lysates as prepared above for GAA assay. Samples were analyzed in duplicates by adding 4 µL of lysate to 36 µL water with and without 10 µL of 800 units/mL of amyloglucosidase enzyme (Sigma) and incubated for 1 hour at 50° C. The reaction was stopped by heat inactivation at 100° C. for 10 min. Finally 200 µL of glucose reagent was added to estimate the amount of glucose released at 340 nm absorbance on Spectramax. A glycogen standard curve ranging from 400 µg/mL to 5 µg/mL was run each day for conversion of absorbance data to absolute glycogen levels. Data are ultimately expressed as µg of glycogen cleaved/milligram of protein. The protein levels were measured in lysates (before denaturing) using Micro BCA Protein Assay Kit according to the manufacturer's instructions.

As illustrated in FIGS. 1A and 1B, glycogen accumulation (determined using the aforementioned biochemical assay) in samples from heart tissue and gastrocnemius tissue of hP545L GAA Tg/KO mice expressing "Moderate" GAA levels having genotype Tg+/+ or Tg+/− were 2-3-fold above the level of glycogen accumulation of wild-type (WT) mice. Likewise, as illustrated in FIGS. 1C and 1D, glycogen accumulation (determined using the aforementioned biochemical assay) in samples from heart tissue and gastrocnemius tissue of hP545L GAA Tg/KO mice expressing "Low" GAA levels having genotype Tg+/+ or Tg+/− were 6-10-fold above the level of glycogen accumulation of wild-type (WT) mice.

Histological Assay for Determining Glycogen Level

Paraffin-embedded tissue sections were cut at 5 µm thickness, mounted onto Superfrost Plus, de-paraffinized in Xylene and finally re-hydrated through graded ethanol series to water. Sections were then treated with 0.1% Periodic acid for 5 min, rinsed with tap water (5 sec.) and stained with Schiff's reagent for 15 min. Excess stain was removed by washing in deionized water for 5 sec. followed by tap water for 10 min, and counterstained with Mayer's Hematoxylin solution (Sigma) before mounting on Xylene based media.

As illustrated in FIGS. 2A-2F, the level of glycogen accumulation (determined using the aforementioned histological assay) in samples from heart tissue and gastrocnemius tissue of hP545L GAA Tg/KO mice expressing "Moderate" or "Low" GAA levels were similar to those levels detected biochemically, as illustrated in FIGS. 1A-1D, wherein glycogen accumulation was at a level 2-3-fold and 6-10-fold, respectively, above that of wild-type (WT) mice.

Histological Assay for Determining Lysosomal Proliferation

Tissues were harvested, processed and sectioned as described above for PAS staining. The endogenous HRP activities were blocked in 3% H2O2/PBS for 60 min followed by washing in PBS for 10 min. Samples were then blocked by Rodent Block M (Biocare Medical) by incubation at room temperature for 30 min, followed by PBS wash (2×5 min). Primary LAMP1 antibody (Abcam, clone 1D4B) was diluted in background sniper (1:1000) and incubated overnight at 4 C. The unbound antibody was washed with PBS (5×5 min) and secondary Rat HRP Polymer (Biocare Medical) was added at room temperature for 10 min. Finally sections were washed in PBS (5×5 min), counterstained with Mayer's Hematoxylin solution (Sigma) and finally developed with Betazoid DAB Kit (room temperature for 5 min).

As illustrated in FIGS. 3A-3F, the level of lysosomal proliferation (determined using the aforementioned histological assay) in samples from heart tissue and gastrocnemius tissue of hP545L GAA Tg/KO mice expressing "Moderate" or "Low" GAA levels was significantly increased relative to that of wild-type (WT) mice. However, the level of lysosomal proliferation in samples from heart tissue and gastrocnemius tissue of hP545L GAA Tg/KO mice expressing "Moderate" GAA levels was lower than that observed in samples from hP545L GAA Tg/KO mice expressing "Low" GAA levels.

GAA Protein Level by Western Blotting

Tissue lysates (50 µg total protein per lane) were subjected to SDS-PAGE on 12% gels (Bio-Rad, Hercules, Calif.), transferred to PVDF membranes (Bio-Rad), and immunoblotted with a rabbit anti-human GAA (kind gift of Dr. Barry Byrne) polyclonal antibody (1:500 dilution). Protein bands were detected using peroxidase-conjugated goat anti-rabbit secondary antibodies (1:1000) (Jackson Immunosearch Labs, West Grove, Pa.) in combination with enhanced chemiluminescence (Pierce). The blots were scanned on an Image Station 4000R using Molecular Imaging Software, version 4.0.

As illustrated in the insets of FIGS. 4A-F, administration of DNJ to hP545L GAA Tg/KO mice expressing "Moderate" GAA levels led to a dose-dependent increase in GAA protein levels as well as the processing of GAA protein to its 76 kDa mature form in disease-relevant tissues.

Testing Agents Useful for the Treatment of Pompe Disease

Daily Dosing Regimen

Eight-week old male hP545L GAA Tg/KO mice were administered DNJ HCl in drinking water (ad libitum) with at least seven (25 g) mice per group. The mice were dosed for 4 weeks with the aim of administering 30 mg/kg/day; 100 mg/kg/day; and 300 mg/kg/day free-base equivalent of DNJ using dosing solutions prepared at 0.15, 0.5 and 1.5 mg/mL free-base equivalent of DNJ, respectively, based on the daily water consumption of transgenic mice (~5 mL/day per mouse). The dosing solutions were made fresh each week and water consumption was monitored daily.

After dosing was completed, mice were euthanized and plasma samples as well as tissue samples harvested as described above. GAA levels and glycogen levels were assayed in samples from disease-relevant tissue of hP545L GAA Tg/KO mice expressing "Moderate" GAA levels which were in the control group (0 mg/kg/day DNJ) or orally dosed with DNJ HCl for 4 weeks with the aim of administering 30, 100, or 300 mg/kg/day free-base equivalent of DNJ as well as wild-type (WT) mice which were not dosed with DNJ. As illustrated in FIGS. 4A-F, administration of DNJ to hP545L GAA Tg/KO mice expressing "Moderate" GAA levels led to a significant and dose-dependent increase in GAA levels. In addition, as illustrated in FIGS. 4A-F, administration of DNJ to hP545L GAA Tg/KO mice expressing "Moderate" GAA levels led to a robust reduction in glycogen levels of soleus, skin, and brain, and a moderate reduction in glycogen levels of heart diaphragm, and gastrocnemius as measured biochemically by amyloglucosidase digestion.

Comparison of Daily and Less-frequent on/Off Dosing Regimens

Eight-week old male hP545L GAA Tg/KO mice expressing "Moderate" GAA levels having genotype Tg+/+ were administered DNJ in drinking water (ad libitum) with fourteen mice per group. Mice were orally dosed (ad libitum in drinking water) either daily or using one of three less-frequent on/off regimens (i.e., (i) 3 days on/4 days off; (ii) 5 days on/2 days off; or (iii) 7 days on/7 days off). Each dosing day, the mice received a dosing solution prepared at 0.5 free-base equivalent of DNJ with the aim of administering 100 mg/kg/day free-base equivalent of DNJ based on the daily water consumption of transgenic mice (~5 mL/day per mouse). The dosing solution was made fresh each week and water consumption was monitored daily. Control groups included eight-week old male hP545L GAA Tg/KO mice expressing "Moderate" GAA levels having genotype Tg+/+ as well as wild-type (WT) mice which were not dosed with DNJ.

After dosing was completed, mice were euthanized and tissue samples harvested as described above. Glycogen levels were assayed in samples from disease-relevant tissue (i.e., heart, diaphragm, gastrocnemius, triceps, brain and spinal cord) of hP545L GAA Tg/KO mice expressing "Moderate" GAA levels which were in the control group (0 mg/kg/day DNJ) or orally dosed (ad libitum in drinking water) with the aim of administering 100 mg/kg/day free-base equivalent of DNJ either daily or using one of three less-frequent on/off regimens (i.e., (i) 3 days on/4 days off; (ii) 5 days on/2 days off; or (iii) 7 days on/7 days off) as well as wild-type (WT) mice which were not dosed with DNJ. As illustrated in FIGS. 5A-F, administration of DNJ to hP545L GAA Tg/KO mice expressing "Moderate" GAA levels led to a significant reduction in glycogen levels (*$p<0.05$ vs. untreated, t-test) in the majority of tissues examined, with the "on/off" regimens resulting in greater glycogen reduction compared to daily administration (#$p<0.05$ daily vs. "on/off", t-test). Collectively, these results indicate that less-frequent DNJ dosing regimens, with less drug administered per week or dosing cycle, can lead to an even greater reduction in the quantity of accumulated substrate.

Additional Agent(s)

It is understood that any of the aforementioned assays for measuring GAA levels or glycogen levels may be used to assess agents useful for the treatment of Pompe disease. The effect of such agents may be tested individually or in combination. Exemplary agents include, but are not limited to, "pharmacological chaperones" such as DNJ, recombinant alpha glucosidase (e.g., Myozyme® (alglucosidase alfa) available from Genzyme), an antineoplastic agent (e.g., Cyclophosphamide, Methotrexate, Rituximab), an antirheumatic agent (e.g., Rituximab), a reproductive control agent (e.g., Methotrexate), or a combination of two or more thereof. Similarly, different therapeutic regimens may be tested for their efficacy in the mouse models provided. Likewise, different modes of administration may be used to deliver the agent(s) (e.g., DNJ may be administered orally, recombinant α-glucosidase may be introduced via intravenous and/or intrathecal infusion).

What is claimed:

1. A mouse model for Pompe disease comprising a knockout transgenic mouse wherein the endogenous alpha-glucosidase gene is disrupted such that the knockout transgenic mouse lacks the capacity to express the gene for mouse alpha-glucosidase and whose genome comprises at least a P545L mutation in a gene encoding human alpha-glucosidase, wherein the amount of human alpha-glucosidase protein expressed and the level of human alpha-glucosidase activity in at least one disease-relevant tissue of the knockout transgenic mouse is in a range of about 3% to about 10% relative to that of a wild-type mouse, where the at least one disease-relevant tissue is selected from the group consisting of: heart, diaphragm, skeletal muscle, skin, and brain.

2. A mouse model for Pompe disease comprising a knockout transgenic mouse wherein the endogenous alpha-glucosidase gene is disrupted such that the knockout transgenic mouse lacks the capacity to express the gene for mouse alpha-glucosidase and whose genome comprises at least a P545L mutation in a gene encoding human alpha-glucosidase, wherein the level of glycogen in at least one disease-relevant tissue of the knockout transgenic mouse is at least 2-fold higher than a wild-type mouse, where the at least one disease-relevant tissue is selected from the group consisting of: heart, diaphragm, skeletal muscle, skin, and brain.

3. A method of screening for a therapeutic agent for Pompe disease, comprising administering a test agent to the knockout transgenic mouse of claim 1 and evaluating the effect of the test agent on at least one of: the amount of alpha-glucosidase protein, the level of alpha-glucosidase activity or the level of glycogen in at least one disease-relevant tissue of the knockout transgenic mouse, wherein at least one of: an increase in the amount of alpha-glucosidase protein, an increase in the level of alpha-glucosidase activity or a reduction in the level of glycogen in at least one disease-relevant tissue relative to a similar knockout transgenic mouse that does not receive the test agent indicates the test agent is therapeutic for Pompe disease.

4. A method for assessing one or more agents for the treatment of Pompe disease, comprising administering one or more agents to the knockout transgenic mouse of claim 1 and evaluating the effect of the agents on at least one of: the amount of alpha-glucosidase protein, the level of alpha-glucosidase activity or the level of glycogen in at least one disease-relevant tissue of the knockout transgenic mouse, wherein at least one of: an increase in the amount of alpha-glucosidase protein, an increase in the level of alpha-glucosidase activity or a reduction in the level of glycogen in at least one disease-relevant tissue as compared to a similar knockout transgenic mouse that does not receive one or more agents is therapeutic for Pompe disease.

5. The method of claim 4 wherein one or more agents is a pharmacological chaperone, a recombinant alpha glucosidase, an antineoplastic agent, an antirheumatic agent, a reproductive control agent, or any combination of two or more thereof.

6. The method of claim 4 wherein one or more agents is DNJ, recombinant alpha glucosidase, Cyclophosphamide, Methotrexate, Rituximab, or any combination of two or more thereof.

7. The method of claim 6 wherein one or more agents includes DNJ and recombinant alpha glucosidase.

8. The method of claim 6 wherein one or more agents includes DNJ.

9. The knockout transgenic mouse of claim 1 wherein the level of glycogen in at least one disease-relevant tissue of the knockout transgenic mouse is at least 2-fold higher than that of a wild-type mouse.

10. A method of screening for a therapeutic agent for Pompe disease, comprising administering a test agent to the knockout transgenic mouse of claim 2 and evaluating the effect of the test agent on at least one of: the amount of alpha-glucosidase protein, the level of alpha-glucosidase activity or the level of glycogen in at least one disease-relevant tissue of the knockout transgenic mouse, wherein at least one of: an increase in the amount of alpha-glucosidase protein, an increase in the level of alpha-glucosidase activity or a reduction in the level of glycogen in at least one disease relevant tissue relative to a similar knockout transgenic mouse that does not receive the test agent indicates the test agent is therapeutic for Pompe disease.

11. A method for assessing one or more agents for the treatment of Pompe disease, comprising administering one or more agents to the knockout transgenic mouse of claim 2 and evaluating the effect of the agents on at least one of: the amount of alpha-glucosidase protein, the level of alpha-glucosidase activity or the level of glycogen in at least one disease-relevant tissue of the knockout transgenic mouse, wherein at least one of: an increase in the amount of alpha-glucosidase protein, an increase in the level of alpha-glucosidase activity or a reduction in the level of glycogen in at least one disease-relevant tissue as compared to a similar knockout transgenic mouse that does not receive one or more agents is therapeutic for Pompe disease.

\* \* \* \* \*

SEQUENCE LISTING

```
<160> NUMBER OF SEQ ID NOS: 6

<210> SEQ ID NO 1
<211> LENGTH: 1980
<212> TYPE: DNA
<213> ORGANISM: Artificial Sequence
<220> FEATURE:
<223> OTHER INFORMATION: gene encoding P545L mutated human
      alpha-glucosidase protein

<400> SEQUENCE: 1
atgggagtga ggcacccgcc ctgctcccac cggctcctgg ccgtctgcgc cctcgtgtcc      60
ttggcaaccg ctgcactcct ggggcacatc ctactccatg atttcctgct ggttccccga     120
gagctgagtg gctcctcccc agtcctggag gagactcacc cagctcacca gcagggagcc     180
agtagaccag ggccccggga tgcccaggca caccccggcc gtcccagagc agtgcccaca     240
```

```
cagtgcgacg tcccccccaa cagccgcttc gattgcgccc ctgacaaggc catcacccag      300
gaacagtgcg aggcccgcgg ctgttgctac atccctgcaa agcagggggct gcagggagcc     360
cagatggggc agccctggtg cttcttccca cccagctacc ccagctacaa gctggagaac      420
ctgagctcct ctgaaatggg ctacacggcc accctgaccc gtaccacccc caccttcttc      480
cccaaggaca tcctgaccct gcggctggac gtgatgatgg agactgagaa ccgcctccac      540
ttcacgatca agatccagc taacaggcgc tacgaggtgc ccttggagac cccgcatgtc       600
cacagccggg caccgtcccc actctacagc gtggagttct ccgaggagcc cttcggggtg      660
atcgtgcgcc ggcagctgga cggccgcgtg ctgctgaaca cgacggtggc gcccctgttc      720
tttgcggacc agttccttca gctgtccacc tcgctgccct cgcagtatat cacaggcctc      780
gccgagcacc tcagtcccct gatgctcagc accagctgga ccaggatcac cctgtggaac      840
cgggaccttg cgcccacgcc cggtgcgaac ctctacgggt ctcacccttt ctacctggcg      900
ctggaggacg cgggtcggc acacggggtg ttcctgctaa acagcaatgc catggatgtg       960
gtcctgcagc cgagccctgc ccttagctgg aggtcgacag gtgggatcct ggatgtctac      1020
atcttcctgg gccagagcc caagagcgtg gtgcagcagt acctggacgt tgtgggatac      1080
ccgttcatgc cgccatactg gggcctgggc ttccacctgt gccgctgggg ctactcctcc     1140
accgctatca cccgccaggt ggtggagaac atgaccaggg cccacttccc cctggacgtc     1200
cagtggaacg acctggacta catggactcc cggagggact tcacgttcaa caaggatggc    1260
ttccgggact tccggccat ggtgcaggag ctgcaccagg cggccggcg ctacatgatg       1320
atcgtggatc ctgccatcag cagctcgggc cctgccggga gctacaggcc ctacgacgag    1380
ggtctgcgga ggggggtttt catcaccaac gagaccggcc agccgctgat tgggaaggta   1440
tggcccgggt ccactgcctt ccccgacttc accaacccca cagccctggc ctggtgggag    1500
gacatggtgg ctgagttcca tgaccaggtg cccttcgacg gcatgtggat tgacatgaac    1560
gagccttcca acttcatcag gggctctgag gacggctgcc ccaacaatga gctggagaac   1620
ccacccctacg tgcttgggt ggttggggggg accctccagg cggccaccat ctgtgcctcc   1680
agccaccagt ttctctccac acactacaac ctgcacaacc tctacggcct gaccgaagcc    1740
atcgcctccc acagggcgct ggtgaaggct cggggggacac gcccatttgt gatctcccgc    1800
tcgacctttg ctggccacgg ccgatacgcc ggccactgga cggggacgt gtggagctcc    1860
tgggagcagc tcgcctcctc cgtgccagaa atcctgcagt ttaacctgct gggggtgcct   1920
ctggtcgggg ccgacgtctg cggcttcctg ggcaacacct cagaggagct gtgtgtgcgc    1980
```

<210> SEQ ID NO 2
<211> LENGTH: 952
<212> TYPE: PRT
<213> ORGANISM: Artificial Sequence
<220> FEATURE:
<223> OTHER INFORMATION: P545L mutated human alpha-glucosidase protein

<400> SEQUENCE: 2

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60
```

-continued

```
Pro Arg Asp Ala Gln Ala His Pro Gly Arg Pro Arg Ala Val Pro Thr
 65                  70                  75                  80

Gln Cys Asp Val Pro Asn Ser Arg Phe Asp Cys Ala Pro Asp Lys
                 85                  90                  95

Ala Ile Thr Gln Glu Gln Cys Glu Ala Arg Gly Cys Cys Tyr Ile Pro
                    100                 105                 110

Ala Lys Gln Gly Leu Gln Gly Ala Gln Met Gly Gln Pro Trp Cys Phe
                115                 120                 125

Phe Pro Pro Ser Tyr Pro Ser Tyr Lys Leu Glu Asn Leu Ser Ser Ser
            130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
                260                 265                 270

Trp Thr Arg Ile Thr Leu Trp Asn Arg Asp Leu Ala Pro Thr Pro Gly
            275                 280                 285

Ala Asn Leu Tyr Gly Ser His Pro Phe Tyr Leu Ala Leu Glu Asp Gly
        290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
                340                 345                 350

Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Thr
        370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495
```

```
Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
            515                 520             525

Ser Glu Asp Gly Cys Pro Asn Asn Glu Leu Glu Asn Pro Pro Tyr Val
    530                 535                 540

Leu Gly Val Val Gly Gly Thr Leu Gln Ala Ala Thr Ile Cys Ala Ser
545             550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625             630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705             710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Val Glu Ala Leu Gly
    770                 775                 780

Ser Leu Pro Pro Pro Ala Ala Pro Arg Glu Pro Ala Ile His Ser
785             790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865             870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
```

```
                915                 920                 925
Ser Pro Asp Thr Lys Val Leu Asp Ile Cys Val Ser Leu Leu Met Gly
            930                 935                 940

Glu Gln Phe Leu Val Ser Trp Cys
945                 950

<210> SEQ ID NO 3
<211> LENGTH: 1980
<212> TYPE: DNA
<213> ORGANISM: Homo sapiens

<400> SEQUENCE: 3
atgggagtga ggcacccgcc ctgctcccac cggctcctgg ccgtctgcgc cctcgtgtcc      60
ttggcaaccg ctgcactcct ggggcacatc ctactccatg atttcctgct ggttccccga     120
gagctgagtg gctcctcccc agtcctggag gagactcacc cagctcacca gcagggagcc     180
agtagaccag gccccgggga tgcccaggca caccccggcc gtcccagagc agtgcccaca     240
cagtgcgacg tccccccaa cagccgcttc gattgcgccc ctgacaaggc catcacccag     300
gaacagtgcg aggcccgcgg ctgttgctac atccctgcaa agcaggggct gcagggagcc     360
cagatggggc agccctggtg cttcttccca cccagctacc ccagctacaa gctggagaac     420
ctgagctcct ctgaaatggg ctacacggcc accctgaccc gtaccacccc cacctactcc     480
cccaaggaca tcctgaccct gcggctggac gtgatgatgg agactgagaa ccgcctccac     540
ttcacgatca agatccagc taacaggcgc tacgaggtgc ccttggagac cccgcatgtc     600
cacagccggg caccgtcccc actctacagc gtggagttct ccgaggagcc cttcggggtg     660
atcgtgcgcc ggcagctgga cggcgcgtg ctgctgaaca cgacggtggc gcccctgttc     720
tttgcggacc agttccttca gctgtccacc tcgctgccct cgcagtatat cacaggcctc     780
gccgagcacc tcagtcccct gatgctcagc accagctgga ccaggatcac cctgtggaac     840
cgggaccttg cgcccacgcc cggtgcgaac ctctacgggt ctcacccttt ctacctggcg     900
ctggaggacg gcgggtcggc acacggggtg ttcctgctaa acagcaatgc catggatgtg     960
gtcctgcagc cgagccctgc ccttagctgg aggtcgacag gtgggatcct ggatgtctac    1020
atcttcctgg gcccagagcc caagagcgtg gtgcagcagt acctggacgt tgtgggatac    1080
ccgttcatgc cgccatactg gggcctgggc ttccacctgt gccgctgggg ctactcctcc    1140
accgctatca cccgccaggt ggtggagaac atgaccaggg cccacttccc cctggacgtc    1200
cagtggaacg acctggacta catggactcc cggagggact tcacgttcaa caaggatggc    1260
ttccgggact cccggccat ggtgcaggag ctgcaccagg cggccggcg ctacatgatg    1320 atcgtggatc ctgccatcag cagctcgggc cctgccggga gctacaggcc ctacgacgag    1380
ggtctgcgga gggggttttt catcaccaac gagaccggcc agccgctgat tgggaaggta    1440
tggcccgggt ccactgcctt ccccgacttc accaacccca cagccctggc ctggtgggag    1500
gacatggtgg ctgagttcca tgaccaggtg cccttcgacg gcatgtggat tgacatgaac    1560
gagccttcca acttcatcag gggctctgag gacggctgcc caacaatga gctgagaac    1620 ccaccctacg tgcctggggt ggttgggggg acctccagg cggccaccat ctgtgcctcc    1680
agccaccagt ttctctccac acactacaac ctgcacaacc tctacggcct gaccgaagcc    1740
atcgcctccc acagggcgct ggtgaaggct cggggacac gcccatttgt gatctcccgc    1800 tcgaccttg ctgccacgg ccgatacgcc ggccactgga cggggacgt gtggagctcc    1860 tgggagcagc tcgcctcctc cgtgccagaa atcctgcagt ttaacctgct ggggtgcct    1920
```
ctggtcgggg ccgacgtctg cggcttcctg ggcaacacct cagaggagct gtgtgtgcgc    1980

<210> SEQ ID NO 4
<211> LENGTH: 952
<212> TYPE: PRT
<213> ORGANISM: Homo sapiens

<400> SEQUENCE: 4

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr

-continued

```
               370                 375                 380
Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
                435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
                515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
                595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
                755                 760                 765

Leu Gly Thr Trp Tyr Asp Leu Gln Thr Val Pro Val Glu Ala Leu Gly
                770                 775                 780

Ser Leu Pro Pro Pro Ala Ala Pro Arg Glu Pro Ala Ile His Ser
785                 790                 795                 800
```

```
Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
            915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
tacgtattag tcatcgctat                                             20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
attaagtact ctagccttaa                                             20
```